United States Patent [19]

Shambaugh

[11] Patent Number: 5,603,342
[45] Date of Patent: Feb. 18, 1997

[54] APPARATUS FOR CLEANING A FLUID SAMPLE PROBE

[75] Inventor: Charles R. Shambaugh, Coral Gables, Fla.

[73] Assignee: Coulter Corporation, Miami, Fla.

[21] Appl. No.: 496,583

[22] Filed: Jun. 29, 1995

[51] Int. Cl.⁶ ........................................................ G01N 1/14
[52] U.S. Cl. .......................... 134/154; 134/155; 134/170; 134/186; 134/34; 422/100; 436/49; 73/864.22; 73/864.23; 73/864.24
[58] Field of Search ................................ 422/63, 67, 81, 422/100, 104; 436/43, 49, 180; 134/170, 154, 155, 186, 34; 73/864.22, 864.23, 864.24

[56] References Cited

U.S. PATENT DOCUMENTS

| | | | |
|---|---|---|---|
| 4,217,780 | 8/1980 | O'Connell et al. | 73/421 |
| 4,311,484 | 1/1982 | Fosslien | 73/864.21 |
| 4,318,885 | 3/1982 | Suzuki et al. | 422/68 |
| 4,516,437 | 5/1985 | Pedroso et al. | 73/864.22 |
| 4,817,443 | 4/1989 | Champseix et al. | 73/864.22 |
| 4,820,497 | 4/1989 | Howell | 422/63 |
| 5,186,194 | 2/1993 | Kitajima | 134/154 |
| 5,318,359 | 6/1994 | Wakatake | 366/140 |

FOREIGN PATENT DOCUMENTS 2075672  11/1981  United Kingdom .

*Primary Examiner*—Long V. Le
*Attorney, Agent, or Firm*—John T. Winburn

[57] ABSTRACT

A sample probe wash chamber for cleaning the exterior of a sample probe. The probe wash chamber includes an interior threaded passageway between a wash fluid inlet and outlet. The inlet tangentially opens into an annular chamber formed adjacent one end of the threaded passageway. The outlet opens into a second annular chamber formed adjacent the other end of the threaded passageway and has a vacuum applied to it. The outlet can open perpendicularly into the second annular chamber to remove any moisture from the end of the sample probe positioned at the outlet opening. The probe wash chamber and the sample probe are movable with respect to one another and preferably the probe wash chamber is movable over the sample probe for multiple sample aspiration and cleaning operations.

5 Claims, 3 Drawing Sheets

APPARATUS FOR CLEANING A FLUID SAMPLE PROBE

BACKGROUND OF THE INVENTION

This invention relates generally to transferring fluid from a vial with a sample probe without fluid carryover or contamination. More particularly, the invention is directed to a sample probe cleaning device which can be utilized to clean and dry the probe as desired.

Automated blood and blood cell analyzers are well known. These analyzers typically utilize a portion of a whole or pre-prepared blood sample. When the blood sample is taken from a subject, it usually is placed into a vial or test tube.

In some analyzers, a portion or aliquot of the blood sample then is aspirated from the vial by a sample probe. The probe can be moved into a fixed position vial or the vial can be moved to a freed position sample probe. The aspirated aliquot then can be dispensed from the sample probe or aspirated through the sample probe into the analyzer or into a sample preparation bath or a combination of various aspiration and dispensing steps.

In the most simple operation, the sample probe must be thoroughly cleaned and dried between aspirations of different sample aliquots to avoid carryover contamination. If the sample probe dispenses the sample aliquot, then the exterior of the sample probe must be washed and dried to avoid carryover which can adversely affect the volume of the dispensed sample aliquot. In cases of small volumes of sample aliquots, the excess sample carried on the exterior of the sample probe can be a significant volume with respect to or can exceed the volume of the dispensed sample aliquot. The carryover on the sample probe exterior thus can be a significant problem with the operation of a single sample aliquot and between different sample aliquots.

The prior art has provided various solutions to the carryover and contamination problem. Some analyzers include a manual sample probe wiping operation between each sample aliquot aspiration. This solution is not always effective and requires potentially intimate operator contact with the sample fluid and is not readily performable during a multiple-step operation in an analyzer.

In an attempt to solve these problems and to effectively automate the probe cleaning operation, the prior art has developed several types of probe wash chambers having a passageway into which the sample probe is inserted to clean the exterior and in some instances the interior of the sample probe. In general, the probe wash chamber includes a wash fluid input into the passageway and a fluid output or exhaust for removing the fluid once the exterior of the sample probe has been cleaned. The prior art probe wash chambers can leak fluid and also can channel along only one side or a portion of the sample probe which can leave residue on the probe exterior. This can contaminate the operation and also cause carryover problems. In an attempt to avoid the channeling problem, the Assignee of the present invention developed a probe wash chamber which included internal threading in at least a portion of the probe wash chamber passageway. The fluid input to the threaded passageway was at a tangent to the threaded passageway. This threaded passageway improved the sample probe washing operation, but still can allow channeling since the fluid input is not always into a threaded channel or groove and can just as easily be partially or wholly opening into the ridge between the threaded channels.

It therefore would be desirable to provide a method and apparatus for aspirating a precise sample aliquot with a sample probe without contamination and carryover on the sample probe exterior. It further is desired to wash the sample probe exterior while containing the wash fluid within a wash chamber.

SUMMARY OF THE INVENTION

The invention provides a sample probe cleaning method and apparatus for cleaning the exterior of a sample probe. A probe wash chamber includes an interior threaded passageway between a wash fluid inlet and outlet. The inlet tangentially opens into an annular chamber formed adjacent one end of the threaded passageway. The outlet opens into a second annular chamber formed adjacent the other end of the threaded passageway. The outlet can open perpendicularly into the second annular chamber to remove any moisture from the end of the sample probe positioned at the outlet opening. The probe wash chamber and the sample probe are movable with respect to one another and preferably the probe wash chamber is movable over the sample probe for multiple sample operations.

DESCRIPTION OF THE PREFERRED EMBODIMENTS

Figure 1:
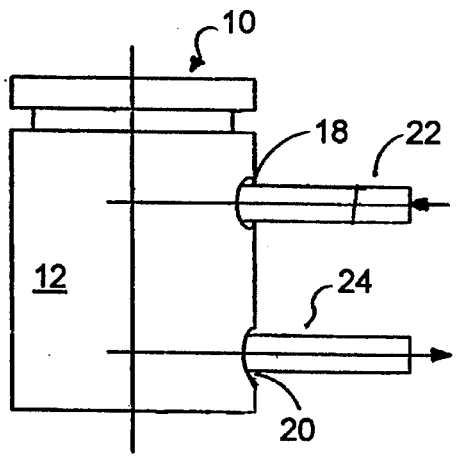
FIG. 1 is a side-plan view of one embodiment of the probe wash chamber of the present invention.
Figure 2:
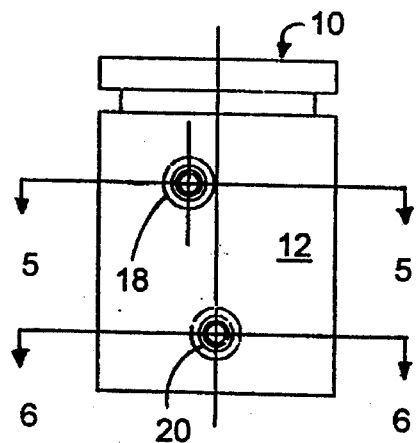
FIG. 2 is a second side-plan view of the probe wash chamber of FIG. 1.
Figure 3:
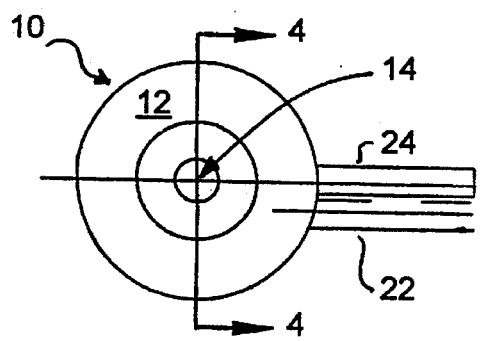
FIG. 3 is a top-plan view of the probe wash chamber of FIG. 1.
Figure 4:
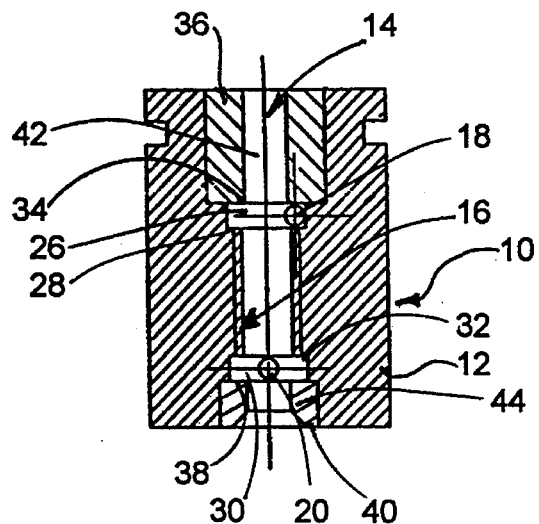
FIG. 4 is a side-sectional view of the probe wash chamber of FIG. 3, taken along the line 4—4 thereof.
Figure 5:
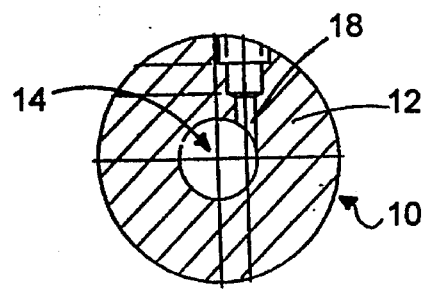
FIG. 5 is a top-sectional view of the probe wash chamber of FIG. 2, taken along the line 5—5 thereof.
Figure 6:
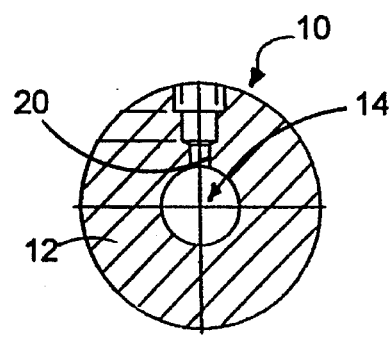
FIGS. 6 is a top-sectional view of the probe wash chamber of FIG. 2, taken along the line 6—6 thereof.

Referring to FIGS. 1–6, a first embodiment of a probe wash device or chamber of the present invention is designated generally by the reference numeral 10. The probe wash chamber 10 includes a body 12 formed from any convenient dimensionally stable material, for example, polysophone, which does not absorb or react with the liquids associated with the probe wash chamber 10.

The body 12 includes a central sample probe washing passageway 14. The passageway 14 includes a threaded portion 16. The probe wash chamber 10 includes an inlet passageway 18 and an outlet passageway 20. The inlet passageway 18 can be coupled to a source of wash fluid, such as a diluent (not illustrated), by a tubing 22 and the outlet passageway 20 can be coupled to a source of vacuum (not illustrated) by a tubing 24. The tubing 22 and 24 can be secured in the respective passageways 18 and 20 by an adhesive, such as any conventional non-soluble adhesive.

The inlet passageway 18 opens tangentially into an annular chamber 26 formed adjacent one end 28 of the threaded passageway 16. The annular chamber 26 and the tangential connection forces the wash fluid to flow around the passageway 14 before entering the threaded passageway 16. This ensures a uniform fluid flow into the threaded passageway 16, without channeling along one side of the threaded passageway 16.

At the exit, the outlet passageway 20 opens into a second annular chamber 30, formed adjacent a second end 32 of the threaded passageway 16. This facilitates the flow of the wash fluid and any residue out of the threaded passageway 16 and into the annular chamber 30 and then out the outlet passageway 20.

An upper wall 34 of the annular chamber 26 is formed by a bushing 36. A lower wall 38 of the annular chamber 30 is formed by a bushing 40. The bushings 36 and 40 are secured to the body 12 by an adhesive, again such as the tubing adhesive. The bushing 36 includes a passageway 42, which forms part of the passageway 44, which also forms part of the passageway 14. The passageway 42 is formed substantially longer than the passageway 44 to ensure that greater air flow is through the passageway 44 to prevent fluid leakage from the probe wash chamber 10.

Figure 7:
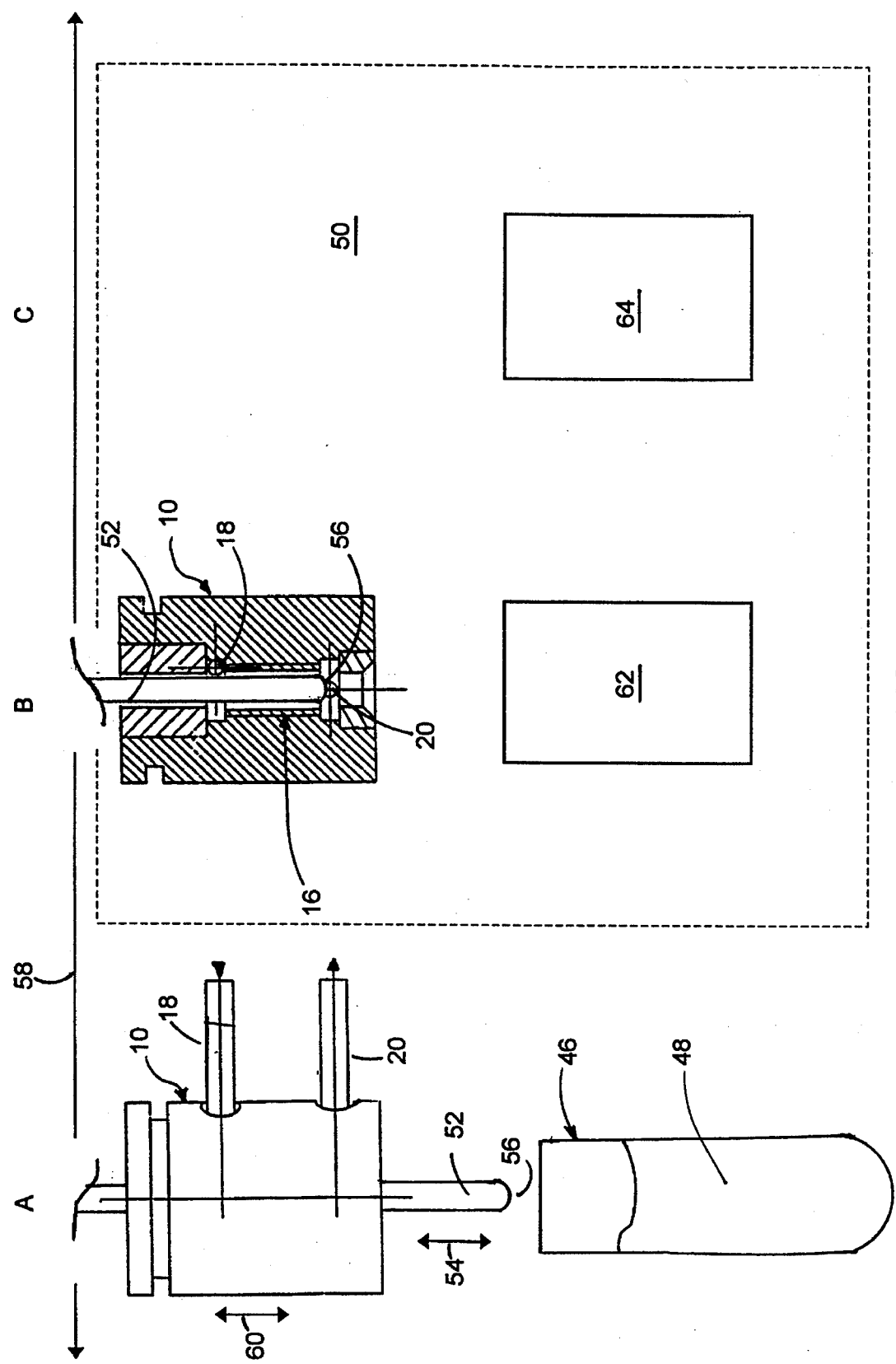
FIG. 7 is a diagrammatical illustration of a preferred operation of the probe wash chamber of the present invention.

Although the probe wash chamber 10 can be fixed or movable with respect to the sample probe, one preferred operation is illustrated diagrammatically in FIG. 7. A sample tube or vial 46 contains a sample fluid 48 such as whole blood. The operation is described for use in a hematology analyzer 50, such as a MicroDiff or MD series, a instrument manufactured by the Assignee of the present invention, Coulter Corporation of Miami, Fla. The probe wash chamber 10 is mounted over a sample probe 52, which can be movable vertically, as illustrated by an arrow 54, to obtain a sample aliquot from the sample 48, or the vial 46 simply can be moved up to the sample probe 52 to obtain the sample aliquot. The sample probe 52 includes an internal aspiration passageway (not illustrated), which has an opening in a tip 56 of the sample probe 52.

The sample probe 52 also is movable horizontally, as indicated by an arrow 58, into the analyzer 50. The sample probe 52 can aspirate and dispense very small volumes of fluid, such as twelve (12) microliters of sample. In that case, the excess blood on the outside of the sample probe 52 can be as great or greater in volume than the sample aliquot to be dispensed. Therefore, it is desirable to clean and dry the outside of the sample probe 52.

The wash fluid, such as a diluent, is provided to the inlet 18, while a vacuum is applied to the outlet 20. The probe wash chamber 10 then is moved down the sample probe 52, as illustrated by an arrow 60, to wash the exterior of the sample probe 52. The tip 56 of the sample probe 52 is stopped adjacent the outlet 20, as shown in position B, which removes all the exterior fluid which has accumulated at the tip 56. The supply of wash fluid to the inlet 18 then is stopped and the probe wash chamber 10 is moved back up to the position shown in position A. The air flow (vacuum) preferably is maintained to dry the exterior of the probe 52.

The sample probe 56 then can be moved downwardly to dispense the sample aliquot into a white blood cell bath 62, where the blood is diluted and the red blood cells are lysed in a conventional manner. While the sample aliquot is being operated on in the bath 62, the sample probe 52 can be moved to a third position C, where a further sample aliquot can be dispensed into a bath 64, which can be a red cell bath. The sample probe 52 also can be moved to a fourth position (not illustrated), where another sample aliquot can be dispensed, for example, for a chemistry test. The operations can be in any desired sequence and, for example, the first sample aliquot in the bath 62 also can be utilized to dilute the sample aliquot to the desired amount. This diluted sample aliquot then can be aspirated from the bath 62 before the lysing operation and delivered to the bath 64.

In one specific embodiment, the threaded portion 16 is threaded at a number 6 screw thread, 32 threads per inch. A vacuum is applied to the exit 20 and the wash fluid is contained within the wash body 12, with and without the presence of the sample probe 52. The length of the bushings 36 and 40 is adjusted so that the greatest amount, such as about eighty-five percent (85%), of the air flow is through the bottom bushing 40. The clearance of the probe 52 and the passageway 16 is on the order of 0.001 inches.

Many modifications and variations of the present invention are possible in light of the above teachings. The exit passageway 20 can also be formed tangentially or at another angle to remove the wash fluid if residue on the probe tip 56 is not of concern. The vacuum level is set depending upon the dimensions of the wash body 12. The rounded shape of the probe tip 56 is preferred for easy cleaning, but can vary if desired. Further, the probe wash chamber 10 can be utilized to wash the exterior of the sample probe 52, without drying the exterior if desired. The movement of the sample probe 52 and/or the probe wash 10, preferably is precise and smooth and preferably can be driven by one or more stepper motors (not illustrated). The aspiration operation also preferably is precisely controlled, such as by a stepper motor driven syringe (not illustrated). It is therefore to be understood that within the scope of the appended claims, the invention may be practiced otherwise than is specifically described.

What is claimed is:

1. In an apparatus for cleaning an exterior surface of a fluid sample probe, said apparatus comprising a probe-cleaning body having (i) an endless wall defining an elongated passageway having a predetermined diameter adapted to receive an elongated, cylindrically-shaped fluid sample probe, said endless wall having a screw-threaded channel formed therein for entraining a cleaning fluid about the exterior surface of the probe located within the passageway, such entrained cleaning fluid being adapted to wash the exterior surface of the probe when relative movement is produced between the probe and probe-cleaning body, the improvement comprising: means defining a first endless annular chamber in said endless wall at one end of said passageway, said first endless annular chamber having a diameter greater than said predetermined of said predetermined of said passageway and being in fluid communication with said screw-threaded channel and encircling the probe located within said passageway; means for introducing cleaning fluid into said first endless annular chamber and means for removing said cleaning fluid at an opposite end of said one end of said passageway.

2. Apparatus as defined by claim 1 wherein said introducing means comprises: means defining an inlet passageway in said endless wall for introducing the cleaning fluid tangentially into said first endless annular chamber.

3. Apparatus as defined by claim 1 further comprising means defining a second endless annular chamber in said endless wall, said second endless annular chamber being located at the opposite end of said passageway and being in fluid communication with said screw-threaded channel.

4. Apparatus as defined by claim 3 further comprising means defining an outlet passageway in said endless wall for allowing cleaning fluid in said second endless annular chamber to exit therefrom.

5. Apparatus as defined by claim 4 wherein said outlet passageway extends in a direction perpendicular to a longitudinal axis of said passageway.

\* \* \* \* \*